United States Patent [19]

Sudo et al.

[11] Patent Number: 5,266,460
[45] Date of Patent: Nov. 30, 1993

[54] METHOD OF PREPARING IMMUNOLOGICAL ANALYTICAL ELEMENT

[75] Inventors: Yukio Sudo; Nobuhito Masuda, both of Saitama, Japan

[73] Assignee: Fuji Photo Film Co., Ltd., Tokyo, Japan

[21] Appl. No.: 887,425

[22] Filed: May 20, 1992

Related U.S. Application Data

[63] Continuation of Ser. No. 630,412, Dec. 19, 1990, abandoned, which is a continuation of Ser. No. 169,310, Mar. 17, 1988, abandoned.

[30] Foreign Application Priority Data

Mar. 17, 1987 [JP] Japan .................... 62-61891

[51] Int. Cl.$^5$ .................. C12Q 1/25; G01N 33/535
[52] U.S. Cl. .................... 435/7.9; 422/56; 422/57; 422/58; 435/7.92; 435/969; 435/970
[58] Field of Search .................... 422/56–58; 435/7.2, 7.72, 970, 7.9, 7.92, 969

[56] References Cited

U.S. PATENT DOCUMENTS

| | | | |
|---|---|---|---|
| 3,992,158 | 11/1976 | Przybylowicz et al. | 435/28 |
| 4,042,335 | 8/1977 | Clément | 422/56 |
| 4,168,146 | 9/1979 | Grubb et al. | 422/56 |
| 4,258,001 | 3/1981 | Pierce et al. | 422/56 |
| 4,447,529 | 5/1984 | Greenquist et al. | 422/56 |

*Primary Examiner*—Jill A. Johnston
*Attorney, Agent, or Firm*—McAulay Fisher Nissen Goldberg & Kiel

[57] ABSTRACT

A method of preparing a dry-type analytical element for immunoassay having at least one water-permeable porous layer and containing a labeled antigen and an antibody to said labeled antigen and to an unlabeled antigen as the components participating in antigen-antibody reaction in said porous layer, which comprises applying or impregnating a first composition containing one of said labeled antigen and said antibody and thereafter applying or impregnating a second composition containing the other of said labeled antigen and said antibody dissolved or suspended in a solvent not dissolving substantially said labeled antigen or said antibody in the first composition onto said porous layer.

6 Claims, 1 Drawing Sheet

METHOD OF PREPARING IMMUNOLOGICAL ANALYTICAL ELEMENT

This is a continuation of application Ser. No. 07/630,412, filed Dec. 19, 1990, and now abandoned which, in turn, is a continuation of application Ser. No. 07/169,310, filed Mar. 17, 1988, now abandoned.

BACKGROUND OF THE INVENTION

1. Field of the Invention

This invention relates to a method for preparing an analytical element useful for immunoassay utilizing antigen-antibody reaction.

2. Description of the Prior Art

Recently, an analytical method using a dry-type analytical element has been developed. In a dry-type analytical element, generally, an analyte such as a biochemical substance contained in a body fluid is allowed to react with reagent(s) incorporated in the analytical element. The amount of a particular reaction product or unreacted component is then determined by measuring the coloring, discoloring, fluorescence, emission or the like, optically such as by spectrophotometry, to determine the content of the analyte. By using the dry-type analytical element, a particular component such as a biochemically active substance in a liquid sample can be analyzed simply, rapidly and accurately.

On the other hand, an immunoassay utilizing a dry-type analytical element has been reported in U.S. Pat. No. 4,459,358, Japanese Patent KOKAI 49-53888 and 59-102388.

The antigen-antibody reaction in the field of immunology is the reaction in which an antibody or antigen specifically reacts with the corresponding antigen or antibody alone. It is widely utilized for the diagnosis of diseases of the autoimmune system, detection of a trace component in a living body and the like. However, since methods utilizing an antigen-antibody reaction requires significant operational skills, it has been desired in the field of clinical tests to develop a measuring method requiring only simple operations which produces accurate results.

The method of measuring an antigen disclosed in Japanese Patent KOKAI 59-77356 (1984) is a typical method utilizing a multilayer analytical element. This analytical element is composed of a spreading layer containing an antigen labeled with a fluorescent material, a partition layer composed of a porous medium and a reaction layer containing an immobilized antibody. The amount of the antigen is determined in this element by measuring the decrease of fluorescence intensity, utilizing the competitive antigen-antibody reactions between the antigen in a sample solution and the labeled antigen.

As another immunoassay method having a relatively high sensitivity, enzyme immunoassay (EIA) is known. A typical EIA is the competitive reaction solid phase method comprising allowing the antigen to be measured and an enzyme-labeled antigen or its derivative to react competitively with immobilized antibody, conducting bound-free (B/F) separation, and measuring the activity of either the enzyme bound to the antibody or the free enzyme to determine the amount of the antigen to be measured. In order to eliminate, the B/F separation, the enzyme whose activity increases or decreases by binding to the antibody is necessary.

In order for these measuring systems to work effectively, two components, i.e. the enzyme-labeled antigen or its derivative and the immobilized antibody in one case, or enzyme labeled antibody or its derivative and immobilized antigen in the other case, are necessary. In either case, these two components should be separated so as to not react with each other before measuring. Satisfactory analytical sensitivity was not obtained in most of the known dry-type analytical elements because of a low signal/background ratio caused by insufficient separation of the two components.

SUMMARY OF THE INVENTION

An object for the invention is to provide a method of preparing an immunological analytical element having a high analytical sensitivity and accuracy.

Such an object has been achieved by preparing a dry-type analytical element for measuring an enzyme activity having at least one water-permeable porous layer and containing a labeled antigen and an antibody to said labeled antigen and to an unlabeled antigen as the components participating in the antigen-antibody reaction in said porous layer, more specifically, the method comprises applying onto said porous layer or impregnating said porous layer with a first composition containing, one of said labeled antigen and said antibody and thereafter applying or impregnating a second composition containing the other of said labeled antigen and said antibody dissolved or suspended in a solvent not capable of dissolving substantially said labeled antigen or said antibody in the first composition.

DETAILED DESCRIPTION OF THE INVENTION

Figure 1:
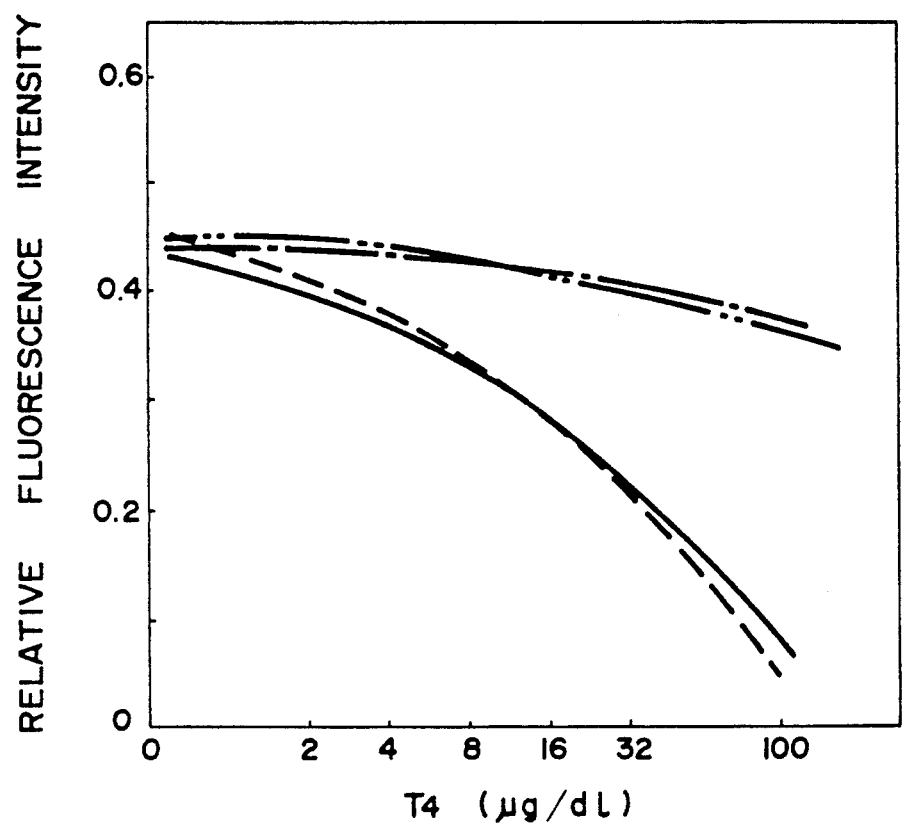
FIG. 1 depicts calibration curves for the analytical elements prepared in Example 1.

The first composition contains the labeled antigen or the antibody to the labeled antigen and to an unlabeled antigen and a solvent.

The labeled antigen should react with the antibody to bind to it, and it is usually the same antigen as the unlabeled antigen.

The label substance may be fluorescent materials, luminescent materials, enzymes, and other known labels used for immunoassay.

The fluorescent materials include the fluorescent materials having amino group such a 1-aminostilbene, 2-aminonaphthalene, p,p'-diaminostilbene, 2-aminoacridine, p,p'-diaminobenzophenone imines, bis-3-aminopyridinium salts and indoles and fluorescent phenols such as 7-hydroxycoumalins, 3,6-dihydroxyxanthenes, tetracycline and salicylic acid esters. A representative fluorescent material is fluorescein.

The luminescent materials includes chemiluminescent materials such as 2,3-dihydro-1,4-phthlazinediones represented by luminol and 2,4,5-triphenylimidazoles.

Various enzymes can be employed as the label. Suitable enzymes are selected by considering the activity, stability, influence of binding upon the activity, the presence of a simple measuring method of enzyme activity. Examples of the enzyme are described in Table 1 and Table 2 of Japanese Patent KOHYO 56-500901, and representative enzymes are glucose oxidase (GOD), $\beta$-D-galactosidase, peroxidase (POD), alkaline phosphatase (ALP), $\alpha$-amylase, luciferase, etc.

The binding method of the label substance to the antigen may be conventional as described, for example, in "Koso-Meneki Sokutei-Ho (Enzyme Immunoassay) (2nd. Ed.)" (Ishikawa et al., 1982), "Rinsho Kensa Gijutsu Zensho 4, Meneki Kassei Kensa (Clinical Assay Technique Complete Book 4 Immune Serum Assay)", pages 97–102 (Ed. Kawai, Igaku-Shorin, 1977), Biochem. Biophys. Res. Commun., 74, 538 (1977), Clinica Chimica Acta, 83, 161 (1973), etc.

The examples of the labeled antigens are also described in the above references. Specific examples are fluoresce in isocyanate-bound thyroxine (FITC-$T_4$). GOD-bound human immunoglobulin (IgG), ALP-bound IgG, POD-labeled $\alpha$-fetoprotein and the like.

The antibody reacts to bind to the above-mentioned labeled antigen and an unlabeled antigen. The unlabeled antigen is usually the antigen to be measured contained in a sample. The reactive site of the antibody to the above two antigens may be common to or different from each other. That is, when at least one of the above antigens has two or more antigenic determinants, the antibody may react at different sites. The antibody may be a monoclonal antibody. It may also be a pepsin-digestion product of the antibody, such as F(ab')$_2$ or Fab'.

The solvent in the first composition dissolves or suspends the component participating in the antibody reaction, i.e. the labeled antigen or the antibody to the labeled antigen (and also to an unlabeled antigen) incorporated in the first composition. Preferable solvents are those which dissolve the above component, and water is usually the most preferable. Suitable concentrations of the component vary depending on the kind of the component, the kind of the solvent and the like.

The first composition may contain reagents for fluoroimmunoassay, EIA or the like other than the labeled antigen or the antibody to the labeled antigen described above. Such reagents are preferably soluble in the above described solvents and include coloring reagents, buffers, etc.

The buffers suitable for the analytical element of the invention are carbonate buffers, borate buffers, phosphate buffers, Good's buffers, and the like. Such a buffer may be selected with reference to "Tanpakushitsu Koso no Kiso-Jikken-Ho (Fundamental Experimental Method of Proteins, Enzymes)" (Horio et al., Nanko-Do, 1981) Biochemistry, vol. 5, No. 2, pp 467–477, 1966, or the like.

The first composition may also contain the usual additives for known analytical elements such as a surfactant and light-reflective particles.

The second composition contains the other member of the components participating in the antigen-antibody reaction and a solvent. That is, when the first composition contains the labeled antigen, the second composition contains the antibody. Conversely, when the first composition contains the antibody, the second composition contains the labeled antigen.

The solvent in the second composition dissolves or suspends the component participating in the antigen-antibody reaction incorporated in the second composition, and it does not substantially dissolve the component incorporated in the first composition. Preferably, it does not swell the hydrophilic polymeric substances such as protein, and its polarity is different from the solvent in the first composition. Examples of such a solvent are alcohols such as ethanol and methanol, ketones such as acetone and ethers such as ethyl cellosolve. Suitable concentrations of the composition are different according to the kind of the solvent and the like.

The second composition may contain other reagents for fluoroimmunoassay, EIA (enzymatic immunoassay) or the like, and the usual additives of known analytical elements in addition to the component participating in the antigen-antibody reaction incorporated in the first composition. They are preferably soluble in the solvent employed.

On the other hand, the above other reagents and additives may be incorporated on or into the porous layer in a step separate from the incorporation of the first and second compositions. In this case, they may be incorporated prior to applying or immersing i.e., impregnating the first composition. When the other reagents and additives are incorporated after applying or immersing the first composition preferably, the solvent for the reagents and additives has the above properties as the solvent for the second composition.

The analytical element prepared by the method of the invention has at least one water-permeable porous layer. The porous layer may be disposed as the topmost layer or disposed between the topmost layer and the reagent layer. The porous layer may be a spreading layer having a metering action or other layers. The metering action is such that a sample spotted on the spreading layer spreads at a fixed amount per unit area without uneven distribution of any component in the sample in lateral directions. The porous layer may be composed of a fibrous material or a nonfibrous material, and includes woven fabrics such as plain weaves and knitted fabrics such a tricot fabric made of natural, synthetic or semisynthetic fiber, nonwoven fabrics, filter papers, glass fiber filter paper, membrane filters composed of cellulose acetate or the like, bodies formed from agglomerated inorganic or organic particles, etc. Suitable porous layers include the fibrous layers described in U.S. Pat. No. 4,292,272 and EP 0 162 302A and the porous layers described in Japanese Patent KOKAI 49-53888, 58-70163 and 61-4959 and Japanese Patent KOKAI 62-116258, 62-138756, 62-138757 and 62-138758, and woven fabrics and knitted fabrics are particularly preferable. The woven fabrics, etc., may be treated with glow discharge such as disclosed in GB 2 087 074A. Besides, the spreading layer may contain a hydrophilic polymer or a surfactant described in EP 0 162 302A and Japanese patent Application 61-122875, 61-122876 and 61-143754 in order to adjust spreading area, spreading speed and the like.

In the method of the invention, the first composition is first applied or impregnated onto the porous layer, and thereafter the second composition is applied or impregnated onto the same porous layer. The application and the impregnation of both compositions may be carried out by a known method such as dip coating, doctor coating, hopper coating, extrusion coating or curtain coating.

The analytical element prepared by the method of the invention may comprise at least two water-permeable layers containing at least one porous spreading layer. The other layer of the above two water-permeable layers is located on the opposite side to the sample-receiving side of the above porous spreading layer, and the porous spreading layer contains the labeled antigen and the antibody to the labeled antigen and also to an unlabeled antigen as the components participating in the antigen-antibody reaction. In this case, the first composition and the second composition may be first separately applied onto or impregnated into the porous spreading layer, and this spreading layer may thereafter be bound to the other water-permeable layer by the method described in Japanese Patent KOKAI 55-164356 or the like. Also, the porous spreading layer applied or impregnated with the first composition may be bound to the other water-permeable layer by the above method or the like, and thereafter, the second composition may be applied onto the spreading layer.

In addition, the analytical element prepared by the method of the invention may comprise at least two water-permeable porous layers. One of the above two porous layers is a spreading layer, and the other is a reagent layer located on the side of the above spreading layer opposite to the sample-receiving side. The reagent layer contains the labeled antigen and the antibody to the labeled antigen and to an unlabeled antigen as the components participating in the antigen-antibody reaction. In this case, the first composition and the second composition are first separately applied onto or impregnated into the spreading layer, and this spreading layer may be bound to the reagent layer by the above method or the like. Where the label substance is an enzyme, a substrate of the enzyme, an oxidizing agent, a coupler, a buffer, etc. may be incorporated into the reagent layer. Among the above, the substrate must necessarily be incorporated.

In the analytical element prepared by the method of the invention, the spreading layer may also function as reagent layer, or a reagent layer may be independently provided. The reagent layer may be a uniform layer containing a hydrophilic polymer as a binder such as gelatin, its derivatives such as phthalated gelatin, cellulose derivatives such as hydroxymethyl cellulose, agarose, polyacrylamide, polymethacrylamide and copolymers of acrylamide or methacrylamide and various vinyl monomers. The reagent layer may also be composed of a porous material such as disclosed in Japanese Patent KOKAI 58-70163 and 61-4959 and Japanese Patent Application 60-256408, 60-279859, 60-279860 and 60-279861.

One or more other layers may be incorporated into the analytical element of the invention. Examples of such layers include a binding layer, a light-blocking layer and a filtering layer. Moreover, each of the porous the reagent layers mentioned previously may be composed of two or more layers, respectively.

The binding layer is provided in order to adhere the porous layer to another layer, and it is preferably composed of a hydrophilic polymer capable of adhering the porous layer when the polymer is in a wet swollen state. Such a hydrophilic polymer includes gelatin, gelatin derivatives, polyacrylamide and starch. The binding layer may also be provided on the aforementioned reagent layer, another reagent layer, light-blocking layer, filtering layer, water absorption layer, registration layer or the like.

The light-blocking layer blocks the color of the sample spotted on a spreading layer, particularly the red color of hemoglobin in a whole blood sample, when the optically detectable change, such as coloration or discoloration, occurring in the reagent layer, a registration layer or the like is measured by reflection photometry from the opposite side of the spreading layer. In addition, it also functions as a light-reflection or background layer. The light-blocking layer is preferably the water-permeable layer composed of a hydrophilic polymer having a film forming property as a binder wherein light-reflecting particles such as titanium dioxide or barium sulfate are dispersed. Preferable hydrophilic polymers are gelatin, gelatin derivatives, polyacrylamide and the like. The light-reflecting particles may also be incorporated into the spreading layer, the reagent layer, a registration layer or the like in addition to or instead of the light-blocking layer.

The following embodiments are practically employable as the analytical element of the invention containing a light-transmissive water impermeable support:

(1) The spreading layer, the reagent layer and the support, superposed in this order.

(2) The spreading layer, the reagent layer, a registration layer and the support, superposed in this order.

(3) The spreading layer, a light-reflecting layer, the reagent layer and the support, superposed in this order.

(4) The spreading layer, a light-reflecting layer, the reagent layer, a registration layer and the support, superposed in this order.

(5) The spreading layer, the reagent layer, a light-reflecting layer, a registration layer and the support, superposed in this order.

(6) The spreading layer, a first reagent layer, a light-reflecting layer, a second reagent layer and the support, superposed in this order. One or both of the above reagent layers contain the labeled antigen.

(7) The spreading layer, a first reagent layer, a light-reflecting layer, a second reagent layer, a registration layer and the support, superposed in this order. One or both of the above reagent layers contain the labeled antigen.

In the above embodiments of (1) to (5), the reagent layer may be composed of different two or more layers. A water absorption layer may be provided between the reagent layer or the registration layer and the support. In the embodiments of (1) to (3) and (6), a filtering layer may be provided between the reagent layer and the registration layer or the spreading layer. In the above embodiments of (3) to (7), a filtering layer may also be provided between the light-reflecting layer and the registration layer, the spreading layer and the reagent layer, the reagent layer and the registration layer. In the case that the reagent layer is composed of two or more layers, a filtering layer may also be provided between them.

A preferable material for the support is polyethylene terephthalate. In order to increase the adhesive strength, the support may be provided with undercoating layer, or the surface of the support may be treated so as to increase hydrophilic property.

EXAMPLE

EXAMPLE 1

Integral Multilayer Immunological Analytical Element for Thyroxine (1) Preparation of Antithyroxine Antiserum Suspension The following mixture was homogenized by a homogenizer for 1 hour to obtain the antithyroxine antiserum suspension.

| | |
|---|---|
| Anatithroxine antiserum (as lyophilized powder) | 1 ml |
| Octylphenoxypolyethoxyethanol (n = 10) | 0.2 mg |
| Acetone | 100 g |

(2) Preparation of Fluorescein-Labeled Thyroxine Suspension

The fluorescein-labeled thyroxine (FITC-T$_4$) was synthesized according to the method described in Japanese Patent KOKAI 59-170768.

The following mixture was homogenized by a homogenizer for 10 minutes to obtain the FITC-T$_4$ suspension.

| | |
|---|---|
| FITC-T$_4$ | 24 ug |
| Distilled water | 1 ml |
| Ethanol | 99 g |
| Octylphenoxypolyethoxyethanol (n = 10) | 0.1 mg |

(3) Preparation of Analytical Element

The support employed was a colorless transparent film of polyethylene terephthalate (PET) having a thickness of 180 μm on which a subbing was provided. An aqueous gelatin solution was coated on the support so as to obtain a dry thickness of 5 μm on drying. This gelatin layer was moisten with about 30 g/m$^2$ of water, and a tricot fabric composed of PET spun yarn was pressed on it to laminate it as the spreading layer, followed by drying.

The first composition having the content (A1) or (A2) was applied on the spreading layer at a rate of 100 cc/m$^2$, and dried.

| | |
|---|---|
| (A1) FITC-T$_4$ | 24 μg |
| Distilled water | 100 ml |
| Octylphenoxypolyethoxyethanol (n = 10) | 0.1 mg |
| (A2) Antithyroxine antiserum | 10 μl |
| Saccharose | 10 g |
| Octylphenoxypolyethoxyethanol (n = 10) | 0.1 mg |
| Distilled water | 100 ml |

Subsequently, the second composition having the following content (B1), (B2), (B3) or (B4) was applied thereon at the rate of 100 cc/m$^2$ in the relation shown in Table 1, followed by drying to obtain an integral multilayer analytical element for measuring thyroxine (T$_4$).

| | |
|---|---|
| (B1) Antithyroxine antiserum suspension | 1.5 ml |
| Polyvinyl pyrrolidone | 5 g |
| Nonylphenoxypolyethoxyethanol (n = 10) | 0.1 mg |
| Ethanol | 100 ml |
| (B2) FITC-T$_4$ suspension | |
| (B3) The same as (A2) | |
| (B4) The same as (A1) | |

TABLE 1

| Analytical Element | First Composition | Second Composition |
|---|---|---|
| Invention (1) | A1 | B1 |
| Invention (2) | A2 | B2 |
| Comparative (3) | A1 | B3 (=A2) |
| Comparative (4) | A2 | B4 (=A1) |

The analytical elements (1) and (2) were prepared by the method of the invention, and the analytical elements (3) and (4) are comparative ones. That is, in the analytical element (1), the labeled antigen (FITC-T$_4$) in aqueous solution and the antibody in ethanol solution were successively applied on the spreading layer, and in the analytical element (2), the antibody in aqueous solution and the labeled antigen in ethanol suspension were applied on the spreading layer. In contrast in analytical elements (3) and (4), both of the labeled antigen and the antibody were applied in aqueous solution.

(4) Measurement of Thyroxine

A serum was treated with activated carbon to obtain thyroxine (T$_4$)-free serum. T$_4$ was added to this T$_4$-free serum to prepare the sera for calibration containing T$_4$ in various concentrations. Each 5 μl of aqueous 0.1 M Blocker's reagent (sodium dodecylnaphthalenesulfonate) solution and 5 μl of 0.3 M glycin-NaCl-NaOH buffer solution were added to 10 μl of each serum for calibration. The mixture was dropped on the respective analytical elements, and kept at 25° C. for 30 minutes. The analytical element was irradiated with a light source at an excitation wave length of 495 nm, and the reflected fluorescence at the wave length of 525 nm was measured from the PET film side by using a fluorophotometer ("Fluorophotometer 650-10(s)", Hitachi Ltd.). The calibration curves thus obtained are shown in FIG. 1. In the drawing, the full line indicates the analytical element (1) of the invention, and the dotted line indicates the analytical element (2) of the invention. The one-dot chain line indicates the comparative analytical element (3), and the two-dot chain line indicates the comparative analytical element (4). As shown in the drawing, the analytical element of the invention is much more sensitive than the comparative analytical element.

EXAMPLE 2

Integral Multilayer Immunological Analytical Element for Theophylline (1) Incorporation of Labeled Antigen The following A-solution was applied on a PET support having a thickness of 180 μm at a rate of 90 cc/m$^2$, and dried. Subsequently, the B-solution was applied thereon at a rate of 100 cc/m$^2$. A polyester knitted fabric treated with glow discharge was laminated on the support during the setting state of gelatin, and dried.

| | |
|---|---|
| A-Solution | |
| Gelatin | 25 g |
| Surfactant ("Surfactant 10G", Olin) | 2 g |
| Distilled water | 444 g |
| NTB (Nitrotetrazlium Blue) | 3.2 g |
| B-Solution | |
| Gelatin | 20 g |
| Surfactant | 2 g |
| Water | 260 g |
| Citric acid | 3 g |
| 1% Diaphorase solution | 20 g |
| pH 7.7 | |

Subsequently, glucose-6-phosphate dehydrogenase (G6PDH)-labeled theophylline solution (prepared by dissolving Reagent B of the "EMIT", Theophylline 100 Assay Kit Syba, U.S.A. with 12 ml of distilled water containing 5% polyvinyl pyrrolidone) was applied as the first composition on 800 cm$^2$ of the polyester knitted fabric, and dried.

(2) Preparation of Analytical Element

On 800 cm$^2$ of the above polyester knitted fabric, the following antitheophylline antibody suspension was applied as the second composition, and dried to complete an immunological analytical element (5) for theophylline

| | |
|---|---|
| Reagent A of the theophylline 100 assay kit "EMIT" (Ciba, U.S.A.) | Whole amount |

-continued

| | |
|---|---|
| Polyvinyl pyrrolidone | 2 g |
| Methanol | 12 ml |

On the other hand, a comparative immunological analytical element (6) for theophylline was prepared in the same manner as the above immunological analytical element (5), except that the above antitheophylline antibody suspension was replaced by the following antitheophylline antibody solution.

| | |
|---|---|
| Reagent A of the theophylline 100 assay kit "EMIT" (Ciba, U.S.A.) | Whole amount |
| Polyvinyl pyrrolidone | 2 g |
| Distilled water | 12 ml |

(3) Measurement of Theophylline

Respective analytical elements were cut into square pieces having a side of 15 mm, and each piece was interposed between the plastic mounts each having a hole /0 mm in diameter. Each serum calibrator ("EMIT" kit, Ciba) containing 03 2.5, 5, 10, 20 or 40 μg/ml of theophylline was mixed with the buffer solution incorporated in the same kit at the volume ratio of 1:4. Each 10 μm of the mixture was spotted on respective analytical elements (5) and (6), reflection absorbance at the wave length of 540 nm was measured after one minute and five minutes from the spotting by using the analyzer ("Drychem 1000", Fuji Photo Film Co., Ltd.). The results are shown in Table 2 as the difference between the measured reflection absorbance after one minute and that after five minutes.

TABLE 2

| Theophylline Conc. of Serum | ΔOD 540 nm | |
|---|---|---|
| | Invention (5) | Comparative (6) |
| 0 | 0.38 | 0.40 |
| 2.5 | 0.50 | 0.38 |
| 5 | 0.57 | 0.42 |
| 10 | 0.60 | 0.39 |
| 20 | 0.66 | 0.40 |
| 40 | 0.70 | 0.41 |

As shown in the table, in the case of using the analytical element prepared by the method of the invention, a good calibration curve was obtained in the range of 2.5 to 40 μg/ml.

We claim:

1. A method for preparing a dry-type analytical element for immunoassay using an antibody-antigen reaction, said element having at least two water-permeable layers, one of said layers being a porous spreading layer having a sample receiving side, and the other of said layers being located on a side of said spreading layer opposite to the sample-receiving side and being a hydrophilic polymer, and containing a labeled antigen and an antibody to said labeled antigen and to an unlabeled antigen as the components participating in the antigen-antibody reaction which occurs in said spreading layer, which comprises the steps of applying or impregnating on or into the spreading layer, a first composition of an enzyme labeled antigen in water and thereafter, applying or impregnating a second composition in an organic solvent selected from the group consisting of alcohols, ketones, and ethers, on or into the spreading layer, said second composition containing the other of said labeled antigen and said antibody dissolved or suspended in the organic solvent, which solvent does not substantially dissolve said enzyme labeled antigen in the first composition wherein at least either of the first composition or the second composition contains polyvinylpyrrolidone.

2. A method for preparing a dry-type analytical element having at least two water-permeable porous layers, one of said layers a being a spreading layer having a sample receiving side, the other of said layers being a hydrophilic polymer reagent layer located on a side of said spreading layer opposite to the sample-receiving side, and containing a labeled antigen and an antibody to said labeled antigen and to an unlabeled antigen as components which participate in an antigen-antibody reaction in said reagent layer, which comprises the steps of applying or impregnating a first composition of an enzyme labeled antigen in water on or into the porous layer and thereafter applying or impregnating a second composition containing the other of said labeled antigen and said antibody dissolved or suspended in an organic solvent selected from the group consisting of alcohols, ketones and ethers, which solvent does not substantially dissolve said enzyme labeled antigen in the first composition wherein at least either of the first composition or the second composition contains polyvinylpyrrolidone.

3. A method for preparing a dry-type analytical element for immunoassay using an antibody-antigen reaction, said element having at least two water-permeable layers, one of said layers being a porous spreading layer having sample receiving side, and the other of said layers being located on a side of said spreading layer opposite to the sample-receiving side and being a hydrophilic polymer, and containing a labeled antigen and an antibody to said labeled antigen and to an unlabeled antigen as the components participating in the antigen-antibody reaction which occurs in said spreading layer, which comprises the steps of applying or impregnating on or into the spreading layer, a first composition of an enzyme labeled antigen in water and thereafter, applying or impregnating a second composition in an organic solvent selected from the group consisting of methanol, ethanol, acetone and 2-ethoxyethanol, on or into the spreading layer, said second composition containing the other of said labeled antigen and said antibody dissolved or suspended in the organic solvent, which solvent does not substantially dissolve said enzyme labeled antigen in the first composition wherein at least either of the first composition or the second composition contains a hydrophilic polymer.

4. The method of claim 3 wherein the solvent is an alcohol and said alcohol is ethanol.

5. A method for preparing a dry-type analytical element having at least two water-permeable porous layers, one of said layers being a spreading layer having a sample receiving side, the other of said layers being a hydrophilic polymer reagent layer located on a side of said spreading layer opposite to the sample-receiving side, and containing a labeled antigen and an antibody to said labeled antigen and to an unlabeled antigen as components which participate in an antigen-antibody reaction in said reagent layer, which comprises the steps of applying or impregnating a first composition of an enzyme labeled antigen in water on or into the porous layer and thereafter applying or impregnating a second composition containing the other of said labeled antigen and said antibody dissolved or suspended in an organic solvent selected from the group consisting of methanol, ethanol, acetone and 2-ethoxyethanol, which solvent does not substantially dissolve said enzyme labeled antigen in the first composition wherein at least either of the first composition or the second composition contains a hydrophilic polymer.

6. The method of claim 5 wherein the solvent is an alcohol and said alcohol is ethanol.

* * * * *